(12) United States Patent
Tang et al.

(10) Patent No.: US 11,028,102 B2
(45) Date of Patent: Jun. 8, 2021

(54) METHODS OF USING 1-O-ACETYLBRITANNILATONE SPIRO ARYL ISOXAZOLINE COMPOUNDS

(71) Applicant: XI'AN TAIKOMED PHARMACEUTICAL TECHNOLOGY CO., LTD., Xi'an (CN)

(72) Inventors: Yonghong Tang, Xi'an (CN); Minghui Chang, Xi'an (CN); Huafeng Qi, Xi'an (CN); Chengyuan Liang, Xi'an (CN); Xingke Ju, Xi'an (CN); Lei Tian, Xi'an (CN); Yuzhi Liu, Xi'an (CN); Han Li, Xi'an (CN)

(73) Assignee: XI'AN TAIKOMED PHARMACEUTICAL TECHNOLOGY CO., LTD., Xi'an (CN)

( * ) Notice: Subject to any disclaimer, the term of this patent is extended or adjusted under 35 U.S.C. 154(b) by 0 days.

(21) Appl. No.: 16/805,772

(22) Filed: Feb. 29, 2020

(65) Prior Publication Data
US 2020/0199152 A1 Jun. 25, 2020

Related U.S. Application Data

(62) Division of application No. 16/167,598, filed on Oct. 23, 2018, now Pat. No. 10,618,911.

(30) Foreign Application Priority Data

Dec. 15, 2017 (CN) .......................... 201711346227.1

(51) Int. Cl.
C07D 498/10 (2006.01)
A61P 11/06 (2006.01)
A61P 29/00 (2006.01)
C07D 495/04 (2006.01)

(52) U.S. Cl.
CPC ............ C07D 498/10 (2013.01); A61P 11/06 (2018.01); A61P 29/00 (2018.01); C07D 495/04 (2013.01)

(58) Field of Classification Search
CPC ...... A61K 31/424; A61P 11/06; C07D 498/10
See application file for complete search history.

Primary Examiner — Kevin E Weddington

(57) ABSTRACT

A method of inhibiting leukotriene include: administrating a therapeutically effective amount of a compound of chemical formula I or II or a pharmaceutical acceptable salt thereof to a subject,

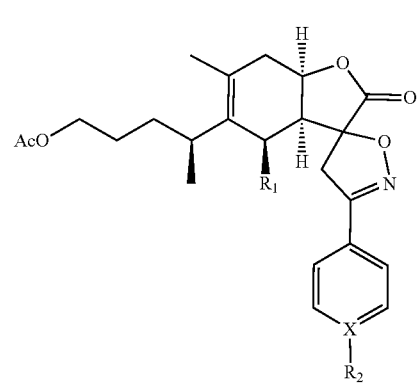

I

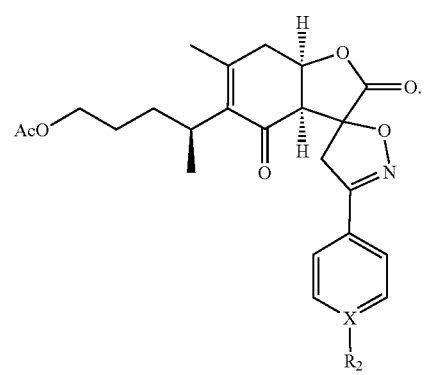

II $R_1$ is OH or OAc; X is C or N; and $R_2$ is H, alkyl, alkoxy, benzyloxy, haloalkyl, OH, CN, $NO_2$, or halogen, provided that when X is N, $R_2$ is nil.

2 Claims, No Drawings

METHODS OF USING 1-O-ACETYLBRITANNILATONE SPIRO ARYL ISOXAZOLINE COMPOUNDS

The present invention is a divisional application of U.S. Ser. No. 16/167,598, filed on Oct. 23, 2018, which claims priority to Chinese Patent Application No. CN 201711346227.1, filed on Dec. 15, 2017, which is incorporated by reference for all purposes as if fully set forth herein.

FIELD OF THE INVENTION

The present invention relates to methods of inhibiting leukotriene, treating asthma, and treating inflammation using 1-O-acetylbritannilatone spiro aryl isoxazoline compounds.

BACKGROUND OF THE INVENTION

*Inula japonica* Thunb/*Inula britannica* L. is a traditional Chinese herbal medicine of the genus *Compositae*. 1-O-acetylbritannilatone is a major component of *Inula japonica* Thunb/*Inula britannica* L. Its acetylated derivative, 1,6-O,O-diacetylbritannilatone, is reported to have some anti-tumor, anti-asthma, anti-inflammatory and other physiological activities.

Inflammation is a common but important basic pathological process, and is the defense response of various tissues with vascular system to various damage factors. Inflammation and many diseases, including rhinitis, rhinitis, arthritis, Alzheimer's, arteriosclerosis, and cancer are all inextricably linked.

Asthma is a complex airway inflammatory process that may be involved in a variety of inflammatory cells. Inflammatory factors, such as Leukotriene C4 ($LTC_4$), are released. Inhibition of $LTC_4$ production is important for controlling asthma and airway inflammation. There is a need to develop novel leukotriene production inhibitors.

SUMMARY OF THE INVENTION

In one embodiment, a method of inhibiting leukotriene include: administrating a therapeutically effective amount of a compound of chemical formula I or II or a pharmaceutical acceptable salt thereof to a subject,

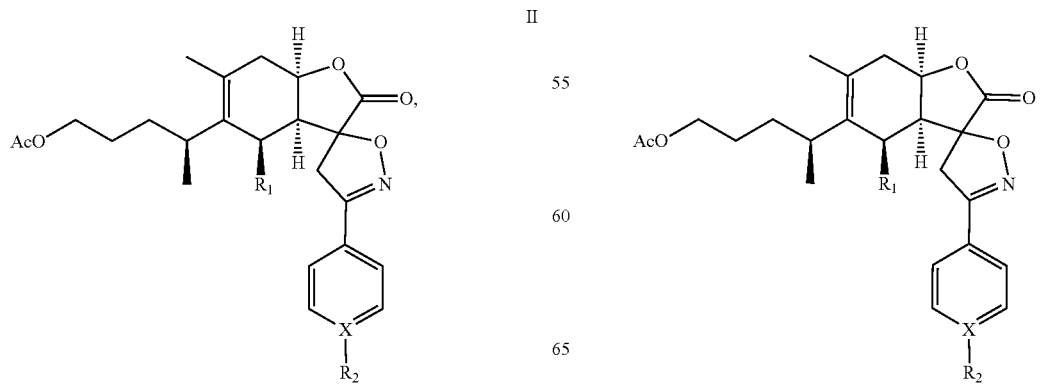

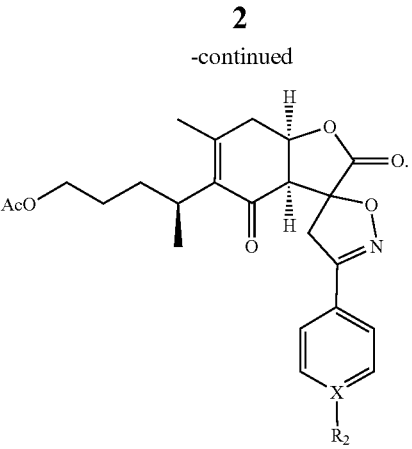

$R_1$ is OH or OAc; X is C or N; and $R_2$ is H, alkyl, alkoxy, benzyloxy, haloalkyl, OH, CN, $NO_2$, or halogen, provided that when X is N, $R_2$ is nil.

In another embodiment, in chemical formula I or II, X is C and $R_2$ is H, F, Cl, Br, CN, $CH_3$, $OCH_3$, $NO_2$ or OH.

In one embodiment, the present invention provides a method treating asthma. The method includes administrating a therapeutically effective amount of the compound of formula I or II or a pharmaceutical acceptable salt thereof to a subject.

In one embodiment, the present invention provides a method of treating inflammation. The method includes administrating a therapeutically effective amount of the compound of formula I or II or a pharmaceutical acceptable salt thereof to a subject.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

The present invention provides a 1-O-acetylbritannilatone spiro aryl isoxazoline compound or a pharmaceutical acceptable salt thereof. The compound has chemical formula I or II:

-continued

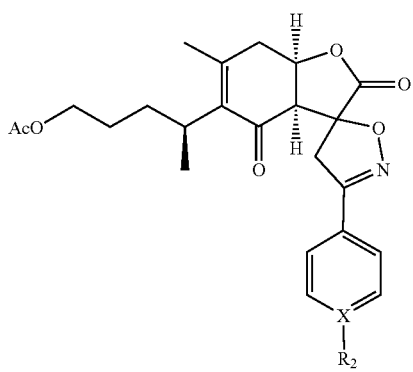

II $R_1$ is OH or OAc; X is C or N; and $R_2$ is H, alkyl, alkoxy, benzyloxy, haloalkyl, OH, CN, $NO_2$, or halogen, provided that when X is N, $R_2$ is nil. Furthermore, in formulas (I) and (II), the spiro carbon is a chiral atom. Compounds of formulas (I) and (II) may be separated into their individual diastereoisomers.

1-O-acetylbritannilatone (ABL) has the following structure:

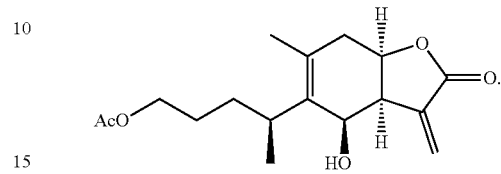

The compound of chemical formula I or II can be prepared in accordance with the following reaction scheme 1.

Scheme 1.

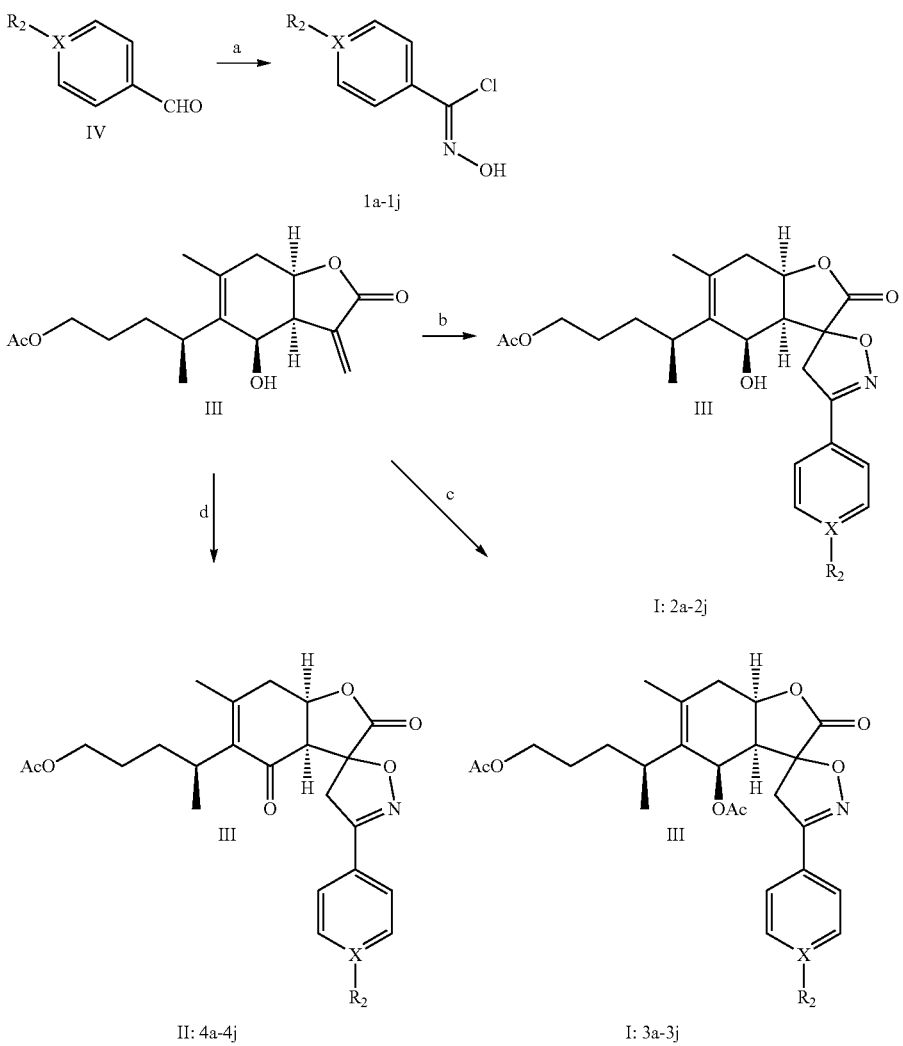

Reagents and condition: (a) 1) NCS, DMF, 40° C.; 2) $NH_2OH \cdot HCl$, $H_2O$, r.t.; (b) 1a-1j, $Et_3N$, $CH_2Cl_2$, r.t.; (c) 1) $Ac_2O$, $Et_3N$, DMAP dry $CH_2Cl_2$, r.t.; 2) 1a-1j, $Et_3N$, $CH_2Cl_2$, r.t.; (d) 1) DMP, $CH_2Cl_2$, r.t.; 2) 1a-1j, $Et_3N$, $CH_2Cl_2$, r.t.;

The substituents of the compounds in Scheme are listed in Table 1 below.

TABLE 1

| Compounds | X | $R_2$ |
|---|---|---|
| 1a-4a | C | H |
| 1b-4b | C | F |
| 1c-4c | C | Cl |
| 1d-4d | C | Br |
| 1e-4e | C | CN |
| 1f-4f | C | $CH_3$ |
| 1g-4g | C | $OCH_3$ |
| 1h-4h | C | $NO_2$ |
| 1i-4i | N | — |
| 1j-4j | C | OH |

A second object of the present invention is to disclose the use of the compounds of formulas I and II in the field of anti-inflammatory and anti-asthmatic. It is characterized in that the compounds inhibit the production of mast cells $LTC_4$. At the test concentrations, the inhibition rates of compounds 2b, 2e, 2h-2j, 3a-3e, 3h-3j, 4c-4e, and 4h-4i exceed 70%. In view of the important role of leukotrienes in the pathogenesis of inflammation and asthma, the above findings show the anti-inflammatory and anti-asthmatic application prospects of the compounds of formulas I and II.

Example 1: Preparation of Compounds 1a-1j

Aryl aldehyde (compound of formula IV in Scheme 1) was dissolved in a mixture of acetonitrile and water (V/V=1:1) in a reaction flask, and hydroxylamine hydrochloride (1.1 equivalents) was added to the reaction flask at room temperature. The reaction was stirred at room temperature and monitored by thin layer chromatograph (TLC). When the reaction was complete, the solvent was removed under reduced pressure to obtain an intermediate. The intermediate was dissolved in dimethylformamide (DMF), and N-chlorosuccinimide (NCS) (1 equivalent) was added in portions to the DMF solution. The reaction solution was stirred at 40° C. and monitored by TLC. When the reaction was complete, ethyl acetate (20 times the reaction mixture) was added to dilute the reaction mixture, and the ethyl acetate solution was washed with water (5×20 mL). Ethyl acetate layer was collected, dried over $MgSO_4$, and concentrated to compounds 1a-1j. Compounds 1a-1j were used in the next step without purification.

Example 2: Preparation of Compounds 2a-2j

Compounds 1a-1j (0.16 mmol) were dissolved in 0.75 mL $CH_2Cl_2$ in a flask. Triethylamine ($Et_3N$) (0.13 mmol) and 1-O-acetylbritannilatone (0.1 mmol) in 0.75 mL $CH_2Cl_2$ were then added. The reaction mixture was stirred at room temperature for 16 hours and monitored by TLC. When the reaction was complete, the reaction mixture was concentrated under reduced pressure to give crude products. The crude products were purified by silica column chromatography (eluting with PE:EA=6:1-3:1, v/v) to give compounds 2a-2j.

2.1

Compound 2a, colorless oil, yield: 44.7%. $^1$H NMR (400 MHz, $CDCl_3$): δ 7.69 (d, J=7.4 Hz, 1.4 Hz, 2H), 7.40-7.47 (m, 3H), 5.17 (m, 1H), 4.13 (s, 1H), 4.01 (t, J=6.3 Hz, 2H), 3.63 (s, 2H), 2.93 (dd, J=5.9 Hz, 2.0 Hz, 1H), 2.72-2.77 (m, 2H), 2.48-2.53 (m, 1H), 2.01 (s, 3H), 1.78 (s, 3H), 1.42-1.57 (m, 2H), 1.19-1.40 (m, 2H), 1.13 (d, J=7.0 Hz, 3H). $^{13}$C NMR (100 MHz, $CDCl_3$): δ 173.00, 171.27, 156.33, 135.52, 130.77, 130.61, 128.86, 128.34, 126.97, 88.89, 76.95, 64.21, 63.92, 50.60, 36.68, 33.88, 33.85, 31.87, 26.99, 20.97, 20.24, 19.74.

2.2

Compound 2a, colorless oil, yield: 82.2%. $^1$H NMR (400 MHz, $CDCl_3$): δ 7.71-7.75 (m, 2H), 7.12-7.17 (d, J=8.0 Hz, 2H), 5.20-5.23 (m, 1H), 4.14 (s, 1H), 4.05 (t, J=6.2 Hz, 2H), 3.64 (s, 2H), 2.96 (dd, J=5.8, 2.1 Hz, 1H), 2.74-2.79 (m, 2H), 2.53-2.58 (m, 1H), 2.05 (s, 3H), 1.81 (s, 3H), 1.42-1.57 (m, 2H), 1.19-1.40 (m, 2H), 1.15 (d, J=6.8 Hz, 3H). $^{13}$C NMR (100 MHz, $CDCl_3$): δ 172.87, 171.34, 164.21 (d, J=250.4 Hz), 155.38, 135.53, 130.53, 129.08, 129.00, 124.64 (d, J=3.4 Hz), 116.20, 115.98, 89.02, 77.08, 64.16, 63.99, 50.49, 36.65, 33.78, 33.77, 31.87, 27.02, 21.02, 20.30, 19.82.

2.3

Compound 2c, colorless oil, yield: 45.9%. $^1$H NMR (400 MHz, $CDCl_3$): δ 7.64 (d, J=8.5 Hz, 2H), 7.40 (d, J=8.5 Hz, 2H), 5.20 (m, 1H), 4.11 (s, 1H), 4.04 (t, J=6.3 Hz, 2H), 3.61 (s, 2H), 2.93 (dd, J=5.8, 2.0 Hz, 1H), 2.72-2.79 (m, 2H), 2.50-2.55 (m, 1H), 2.03 (s, 3H), 1.80 (s, 3H), 1.53-1.62 (m, 2H), 1.33-1.49 (m, 2H), 1.13 (d, J=6.8 Hz, 3H). $^{13}$C NMR (100 MHz, $CDCl_3$): δ 172.80, 171.29, 155.46, 136.80, 135.54, 130.67, 129.16, 128.22, 126.90, 89.26, 64.13, 64.00, 50.51, 36.45, 33.80, 31.86, 27.04, 20.99, 20.26, 19.79.

2.4

Compound 2d, colorless oil, yield: 68.8%. $^1$H NMR (400 MHz, $CDCl_3$): δ 7.58 (s, 4H), 5.19 (m, 1H), 4.12 (s, 1H), 4.06 (t, J=6.2 Hz, 2H), 3.62 (s, 2H), 2.94 (dd, J=4.7, 2.2 Hz, 1H), 2.75 (m, 2H), 2.52-2.57 (m, 1H), 2.03 (s, 3H), 1.79 (s, 3H), 1.42-1.57 (m, 2H), 1.19-1.40 (m, 2H), 1.14 (d, J=7.0 Hz, 3H). $^{13}$C NMR (100 MHz, $CDCl_3$): δ 172.68, 171.21, 155.50, 135.61, 132.11, 130.70, 128.41, 127.39, 125.12, 89.30, 64.08, 50.52, 36.40, 33.81, 31.87, 27.06, 20.95, 20.24, 19.81.

2.5

Compound 2e, colorless oil, yield: 70.5%. $^1$H NMR (400 MHz, $CDCl_3$): δ 7.84 (d, J=8.0 Hz, 2H), 7.73 (d, J=8.0 Hz, 2H), 5.20 (s, 1H), 4.11 (s, 1H), 4.06 (t, J=6.2 Hz, 2H), 3.65 (s, 2H), 2.94 (d, J=4.7 Hz, 1H), 2.77 (m, 2H), 2.50-2.55 (m, 1H), 2.03 (s, 3H), 1.80 (s, 3H), 1.42-1.57 (m, 2H), 1.19-1.40 (m, 2H), 1.13 (d, J=6.8 Hz, 3H). $^{13}$C NMR (100 MHz, $CDCl_3$): δ 172.46, 171.30, 155.17, 135.57, 132.71, 132.58, 130.69, 127.49, 118.13, 114.07, 90.01, 77.22, 64.05, 63.99, 50.41, 35.96, 33.76, 33.72, 31.87, 27.11, 20.98, 20.20, 19.78.

2.6

Compound 2f, colorless oil, yield: 67.6%. $^1$H NMR (400 MHz, $CDCl_3$): δ 7.57 (d, J=8.1 Hz, 2H), 7.22 (d, J=8.1 Hz, 2H), 5.17 (m, 1H), 4.12 (s, 1H), 4.01 (t, J=6.3 Hz, 2H), 3.60 (s, 2H), 2.93 (d, J=5.92, 2.0 Hz, 1H), 2.72-2.77 (m, 2H), 2.47-2.52 (m, 1H), 2.39 (s, 3H), 2.01 (s, 3H), 1.78 (s, 3H), 1.42-1.57 (m, 2H), 1.19-1.40 (m, 2H), 1.12 (d, J=7.0 Hz, 3H). $^{13}$C NMR (100 MHz, $CDCl_3$): δ 173.09, 171.27, 156.27, 141.13, 135.51, 130.58, 129.55, 126.90, 125.50, 88.68, 64.22, 63.92, 50.63, 36.78, 33.90, 33.86, 31.87, 26.98, 21.50, 20.97, 20.24, 19.74.

2.7

Compound 2g, colorless oil, yield: 63.3%. $^1$H NMR (400 MHz, $CDCl_3$): δ 7.63 (d, J=8.8 Hz, 2H), 6.93 (d, J=8.8 Hz, 2H), 5.20 (m, 1H), 4.13 (s, 1H), 4.02 (t, J=6.3 Hz, 2H), 3.60 (s, 2H), 3.48 (s, 2H), 2.93 (dd, J=5.9, 1.9 Hz, 1H), 2.72-2.77 (m, 2H), 2.48-2.53 (m, 1H), 2.02 (s, 3H), 1.79 (s, 3H), 1.42-1.57 (m, 2H), 1.19-1.40 (m, 2H), 1.13 (d, J=7.0 Hz, 3H). $^{13}$C NMR (100 MHz, $CDCl_3$): δ 173.14, 171.29, 161.55, 155.87, 135.54, 130.61, 128.56, 120.83, 114.28, 88.57, 76.90, 64.22, 63.97, 55.39, 50.64, 36.90, 33.90, 33.85, 31.87, 26.99, 20.98, 20.24, 19.76.

2.8

Compound 2h, colorless oil, yield: 60.4%. $^1$H NMR (400 MHz, CDCl$_3$): δ 8.28 (d, J=8.8 Hz, 2H), 7.90 (d, J=8.8 Hz, 2H), 5.20 (m, 1H), 4.11 (s, 1H), 4.05 (t, J=6.2 Hz, 2H), 3.66 (s, 2H), 2.94 (dd, J=5.8, 2.2 Hz, 1H), 2.70-2.77 (m, 2H), 2.52-2.57 (m, 1H), 2.02 (s, 3H), 1.79 (s, 3H), 1.42-1.57 (m, 2H), 1.19-1.40 (m, 2H), 1.12 (d, J=7.0 Hz, 3H). $^{13}$C NMR (100 MHz, CDCl$_3$): δ 172.47, 171.37, 154.97, 148.84, 135.54, 134.43, 130.72, 127.85, 124.09, 90.18, 77.32, 64.06, 63.92, 50.39, 36.00, 33.75, 33.69, 31.87, 27.11, 21.01, 20.28, 19.77.

2.9

Compound 2i, colorless oil, yield: 39.6%. $^1$H NMR (400 MHz, CDCl$_3$): δ 8.71 (d, J=5.7 Hz, 2H), 7.63 (d, J=5.7 Hz, 2H), 5.20 (m, 1H), 4.11 (s, 1H), 4.06 (t, J=6.3 Hz, 2H), 3.64 (s, 2H), 2.96 (dd, J=5.8, 2.2 Hz, 1H), 2.73-2.77 (m, 2H), 2.53-2.57 (m, 1H), 2.03 (s, 3H), 1.80 (s, 3H), 1.42-1.57 (m, 2H), 1.19-1.40 (m, 2H), 1.14 (d, J=7 Hz, 3H). $^{13}$C NMR (100 MHz, CDCl$_3$): δ 173.14, 171.29, 161.55, 155.87, 135.54, 130.61, 128.56, 120.83, 114.28, 88.57, 76.90, 64.22, 63.97, 55.39, 50.64, 36.90, 33.90, 33.85, 31.87, 26.99, 20.98, 20.24, 19.76.

2.10

Compound 2j, colorless oil, yield: 52.6%. $^1$H NMR (400 MHz, DMSO): δ 10.03 (s, 1H), 7.56 (d, J=8.7 Hz, 2H), 6.84 (d, J=8.8 Hz, 2H), 5.12-5.08 (m, 1H), 4.81 (d, J=4.7 Hz, 2H), 4.04 (s, 1H), 3.87 (t, J=6.2 Hz, 2H), 3.78 (d, J=10.5 Hz, 1H), 3.44 (d, J=10.5 Hz, 1H), 3.34 (s, 3H), 2.80 (dd, J=5.8, 2.2 Hz, 1H), 2.72-2.62 (m, 2H), 2.30 (q, J=4.1 Hz, 1H), 1.94 (s, 3H), 1.69 (s, 3H), 1.46-1.40 (m, 2H), 1.14-1.35 (m, 3H), 1.05 (d, J=6.8 Hz, 3H). $^{13}$C NMR (100 MHz, DMSO): δ 173.59, 170.32, 159.64, 156.17, 135.23, 128.60, 127.75, 118.88, 115.64, 87.75, 76.38, 63.77, 62.13, 50.37, 36.75, 33.72, 33.29, 31.09, 26.55, 20.62, 19.74.

Example 3: Preparation of Compounds 3a-3j

1-O-acetylbritannilatone (1 equivalent), 4-dimethylaminopyridine (DMAP) (1.1 equivalents), and acetic anhydride (1.5 equivalents) were dissolved in 6 mL fresh anhydrous CH$_2$Cl$_2$ in a flask. The mixture was reacted at room temperature for 20 minutes monitored. After the reaction was complete, 10 mL ice water was added to the reaction mixture and stirred for 20 minutes. The mixture was then extracted with CH$_2$Cl$_2$ (15 mL×3), and the methylene chloride solution was dried over MgSO$_4$, filtered and concentrated to crude 1,6-O,O-diacetylbritannilatone (OBAL). Crude 1,6-O,O-diacetylbritannilatone was purified by flesh chromatograph for use in the next step. Compounds 1a-1j (0.16 mmol) were dissolved in 0.3 mL CH$_2$Cl$_2$ in a flask. Triethylamine (Et$_3$N) (0.13 mmol) and 1,6-O,O-diacetylbritannilatone (0.1 mmol) in 0.75 mL CH$_2$Cl$_2$ were then added. The reaction mixture was stirred at room temperature for 16 hours and monitored by TLC. When the reaction was complete, the reaction mixture was concentrated under reduced pressure to give crude products. The crude products were purified by silica column chromatography (eluting with PE:EA=6:1-3:1, v/v) to give compounds 3a-3j.

3.1

Compound 3a, light yellow oil, yield: 40.7%. $^1$H NMR (400 MHz, CDCl$_3$): δ 7.73-7.75 (m, 2H), 7.43-7.44 (m, 3H), 5.25 (s, 1H), 5.19-5.22 (m, 1H), 4.03-4.06 (m, 2H), 4.01 (d, J=16.5 Hz, 1H), 3.63 (d, J=16.5 Hz, 1H), 2.83 (d, J=5.8 Hz, 1H), 2.72-2.79 (m, 1H), 2.68 (s, 1H), 2.59-2.64 (m, 1H), 2.03 (s, 3H), 2.01 (s, 3H), 1.85 (s, 3H), 1.51-1.57 (m, 1H), 1.26-1.43 (m, 2H), 1.05-1.08 (m, 1H), 0.92 (d, J=7.0 Hz, 3H). $^{13}$C NMR (100 MHz, CDCl$_3$): δ 172.41, 171.20, 171.00, 156.79, 134.41, 130.90, 130.70, 128.80, 128.39, 127.11, 89.96, 76.91, 64.99, 64.16, 49.48, 36.11, 33.83, 33.73, 32.20, 26.74, 21.16, 20.97, 20.76, 18.54.

3.2

Compound 3b, colorless oil, yield: 75.6%. $^1$H NMR (400 MHz, CDCl$_3$): δ 7.75-7.78 (m, 2H), 7.12-7.17 (m, 2H), 5.23 (s, 1H), 5.2-5.22 (m, 1H), 4.04-4.08 (m, 2H), 4.00 (d, J=16.5 Hz, 1H), 3.63 (d, J=16.5 Hz, 1H), 2.83 (d, J=5.8 Hz, 1H), 2.73-2.80 (m, 1H), 2.69 (s, 1H), 2.61-2.66 (m, 1H), 2.05 (s, 3H), 2.03 (s, 3H), 1.87 (s, 3H), 1.51-1.57 (m, 1H), 1.26-1.43 (m, 2H), 1.05-1.08 (m, 1H), 0.93 (d, J=7.0 Hz, 3H). $^{13}$C NMR (100 MHz, CDCl$_3$): δ 172.36, 171.24, 171.12, 164.07 (d, J=250.1 Hz), 155.88, 134.46, 130.79, 129.23, 129.15, 124.66 (d, J=3.2 Hz), 116.13, 115.91, 89.11, 64.96, 64.13, 49.43, 36.11, 33.77, 33.68, 32.22, 26.76, 21.21, 21.00, 20.79, 18.55.

3.3

Compound 3c, colorless oil, yield: 81.8%. $^1$H NMR (400 MHz, CDCl$_3$): δ 7.69 (d, J=8.5 Hz, 2H), 7.69 (d, J=8.5 Hz, 2H), 5.21 (d, J=3.0 Hz, 1H), 5.21 (s, 1H), 4.00-4.08 (m, 2H), 3.98 (d, J=16.5 Hz, 1H), 3.61 (d, J=16.5 Hz, 1H), 2.81 (d, J=5.8 Hz, 1H), 2.71-2.78 (m, 1H), 2.67 (s, 1H), 2.60-2.65 (m, 1H), 2.03 (s, 3H), 2.01 (s, 3H), 1.85 (s, 3H), 1.51-1.57 (m, 1H), 1.26-1.43 (m, 2H), 1.05-1.08 (m, 1H), 0.92 (d, J=7.0 Hz, 3H). $^{13}$C NMR (100 MHz, CDCl$_3$): δ 172.25, 171.20, 171.09, 155.95, 136.75, 134.42, 130.83, 129.11, 128.38, 126.92, 89.29, 64.95, 64.10, 49.43, 35.91, 33.77, 33.70, 32.22, 26.91, 26.78, 21.17, 20.98, 20.77, 18.54.

3.4

Compound 3d, colorless oil, yield: 69.3%. $^1$H NMR (400 MHz, CDCl$_3$): δ 7.64 (d, J=8.6 Hz, 2H), 7.59 (d, J=8.6 Hz, 2H), 5.21 (d, J=3.0 Hz, 1H), 5.21 (s, 1H), 4.00-4.08 (m, 2H), 3.98 (d, J=16.5 Hz, 1H), 3.61 (d, J=16.5 Hz, 1H), 2.81 (d, J=5.8 Hz, 1H), 2.71-2.78 (m, 1H), 2.67 (s, 1H), 2.60-2.65 (m, 1H), 2.03 (s, 3H), 2.01 (s, 3H), 1.85 (s, 3H), 1.51-1.57 (m, 1H), 1.26-1.43 (m, 2H), 1.05-1.08 (m, 1H), 0.92 (d, J=7.0 Hz, 3H). $^{13}$C NMR (100 MHz, CDCl$_3$): δ 172.23, 171.20, 171.09, 156.05, 134.42, 132.07, 130.83, 128.57, 127.35, 125.11, 89.32, 64.94, 64.09, 49.43, 35.83, 33.77, 33.70, 32.22, 26.91, 26.78, 21.17, 20.99, 20.77, 18.54.

3.5 Preparation of Compound 3e

Compound 3e, colorless oil, yield: 74.8%. $^1$H NMR (400 MHz, CDCl$_3$): δ 7.88 (d, J=8.2 Hz, 2H), 7.74 (d, J=8.2 Hz, 2H), 5.21 (d, J=3.0 Hz, 1H), 5.20 (s, 1H), 4.00-4.13 (m, 2H), 4.00 (d, J=16.2 Hz, 1H), 3.64 (d, J=16.5 Hz, 1H), 2.82 (d, J=5.7 Hz, 1H), 2.61-2.78 (m, 3H), 2.03 (s, 3H), 2.02 (s, 3H), 1.86 (s, 3H), 1.51-1.57 (m, 1H), 1.26-1.43 (m, 2H), 1.05-1.08 (m, 1H), 0.92 (d, J=7.0 Hz, 3H). $^{13}$C NMR (100 MHz, CDCl$_3$): δ 171.95, 171.20, 155.63, 134.45, 132.69, 132.54, 130.78, 127.64, 118.18, 114.07, 89.97, 64.88, 64.01, 49.35, 35.46, 33.71, 33.69, 32.23, 26.85, 21.15, 20.96, 20.75, 18.52.

3.6

Compound 3f, colorless oil, yield: 70.4%. $^1$H NMR (400 MHz, CDCl$_3$): δ 7.64 (d, J=8.2 Hz, 2H), 7.25 (d, J=8.2 Hz, 2H), 5.26 (s, 1H), 5.20-5.22 (m, 1H), 4.05-4.09 (m, 2H), 4.00 (d, J=16.5 Hz, 1H), 3.63 (d, J=16.5 Hz, 1H), 2.83 (d, J=5.8 Hz, 1H), 2.73-2.80 (m, 1H), 2.69 (s, 1H), 2.62-2.67 (m, 1H), 2.05 (s, 3H), 2.03 (s, 3H), 1.87 (s, 3H), 1.51-1.57 (m, 1H), 1.26-1.43 (m, 2H), 1.05-1.08 (m, 1H), 0.94 (d, J=7.0 Hz, 3H). $^{13}$C NMR (100 MHz, CDCl$_3$): δ 172.45, 171.15, 170.90, 156.73, 140.99, 134.36, 130.97, 129.47, 127.04, 125.59, 88.76, 65.04, 64.14, 49.51, 36.22, 33.87, 33.74, 32.19, 26.75, 26.78, 21.47, 21.13, 20.94, 20.73, 18.52.

3.7

Compound 3g, colorless oil, yield: 55.2%. $^1$H NMR (400 MHz, CDCl$_3$): δ 7.70 (d, J=8.8 Hz, 2H), 6.96 (d, J=8.8 Hz, 2H), 5.27 (s, 1H), 5.20-5.23 (m, 1H), 4.07 (t, J=6.2 Hz, 2H), 4.00 (d, J=16.5 Hz, 1H), 3.87 (s, 3H), 3.62 (d, J=16.5 Hz, 1H), 2.83 (d, J=5.8 Hz, 1H), 2.73-2.80 (m, 1H), 2.67 (s, 1H), 2.61-2.66 (m, 1H), 2.05 (s, 3H), 2.03 (s, 3H), 1.87 (s, 3H), 1.51-1.57 (m, 1H), 1.26-1.43 (m, 2H), 1.05-1.08 (m, 1H), 0.94 (d, J=7.0 Hz, 3H). $^{13}$C NMR (100 MHz, CDCl$_3$): δ 172.51, 171.16, 170.90, 161.54, 156.33, 134.36, 130.98, 128.70, 120.95, 114.23, 88.65, 76.83, 65.07, 64.13, 55.37, 49.54, 36.32, 33.87, 33.74, 32.19, 26.77, 21.14, 20.94, 20.73, 18.52.

3.8

Compound 3h, colorless oil, yield: 79.5%. $^1$H NMR (400 MHz, CDCl$_3$): δ 8.30 (d, J=8.9 Hz, 2H), 7.95 (d, J=8.9 Hz, 2H), 5.22-5.24 (m, 1H), 5.20 (s, 1H), 4.05-4.15 (m, 2H), 4.04 (d, J=16.5 Hz, 1H), 3.69 (d, J=16.5 Hz, 1H), 2.84 (d, J=5.7 Hz, 1H), 2.73-2.79 (m, 1H), 2.69 (s, 1H), 2.62-2.67 (m, 1H), 2.04 (s, 3H), 2.02 (s, 3H), 1.86 (s, 3H), 1.51-1.57 (m, 1H), 1.26-1.43 (m, 2H), 1.05-1.08 (m, 1H), 0.93 (d, J=7.0 Hz, 3H). $^{13}$C NMR (100 MHz, CDCl$_3$): δ 171.92, 171.26, 155.43, 148.88, 134.48, 134.43, 130.75, 128.01, 124.06, 90.16, 77.12, 76.91, 64.88, 64.02, 49.33, 35.51, 33.68, 32.25, 26.88, 21.18, 21.00, 20.78, 18.55.

3.9

Compound 3i, colorless oil, yield: 49.7%. $^1$H NMR (400 MHz, CDCl$_3$): δ 8.73 (d, J=5.3 Hz, 2H), 7.65 (d, J=5.4 Hz, 2H), 5.21-5.22 (m, 1H), 5.20 (s, 1H), 4.04-4.10 (m, 2H), 4.00 (d, J=16.5 Hz, 1H), 3.64 (d, J=16.5 Hz, 1H), 2.83 (d, J=5.8 Hz, 1H), 2.73-2.78 (m, 1H), 2.68 (s, 1H), 2.61-2.66 (m, 1H), 2.04 (s, 3H), 2.02 (s, 3H), 1.86 (s, 3H), 1.51-1.57 (m, 1H), 1.26-1.43 (m, 2H), 1.05-1.08 (m, 1H), 0.92 (d, J=7.0 Hz, 3H). $^{13}$C NMR (100 MHz, CDCl$_3$): δ 171.89, 171.24, 171.21, 155.39, 150.24, 136.06, 134.46, 130.79, 121.07, 90.08, 77.09, 64.86, 64.04, 49.35, 35.16, 33.72, 33.70, 32.24, 26.86, 21.17, 20.99, 20.77, 18.54.

3.10

Compound 3j, colorless 3j, yield: 57.1%. $^1$H NMR (400 MHz, CDCl$_3$): δ 7.56 (d, J=8.7 Hz, 2H), 6.82 (d, J=8.7 Hz, 2H), 5.25 (s, 1H), 5.22-5.19 (m, 1H), 4.05 (t, J=5.2 Hz, 2H), 3.95 (d, J=16.4 Hz, 1H), 3.58 (d, J=16.5 Hz, 1H), 2.83 (d, J=5.8 Hz, 1H), 2.79-2.72 (m, 1H), 2.67 (brs, 1H), 2.65-2.60 (m, 1H), 2.04 (s, 3H), 2.03 (s, 3H), 1.85 (s, 3H), 1.51-1.57 (m, 1H), 1.26-1.43 (m, 2H), 1.05-1.08 (m, 1H), 0.92 (d, J=7.0 Hz, 3H). $^{13}$C NMR (100 MHz, CDCl$_3$): δ 172.72, 171.51, 171.40, 158.12, 156.37, 134.57, 130.84, 128.89, 120.64, 115.73, 88.59, 77.23, 65.23, 64.28, 49.48, 36.33, 33.85, 33.72, 32.20, 26.73, 21.23, 21.01, 20.78, 18.54.

Example 4

Dess-Martin periodinane (1.1 equivalents) was dissolved 0.3 mL CH$_2$Cl$_2$ at 0° C. 1-O-acetylbritannilatone (1 equivalent) in 0.6 mL CH$_2$Cl$_2$ was added to the periodinane solution. The mixture was then reacted at room temperature for 18 hours monitored by TLC. After the reaction was complete, the mixture concentrated under reduced pressure to give crude 1-O-acetyl-6-oxobritannilatone. Crude 1-O-acetyl-6-oxobritannilatone was purified by flesh chromatograph (eluting with PE:EA=8:1-4:1, v/v) for use in the next step. Compounds 1a-1j (0.16 mmol) were dissolved in 0.3 mL CH$_2$Cl$_2$ in a flask. Triethylamine (Et$_3$N) (0.13 mmol) and 1-O-acetyl-6-oxobritannilatone (0.1 mmol) in 0.75 mL CH$_2$Cl$_2$ were then added. The reaction mixture was stirred at room temperature for 16 hours and monitored by TLC. When the reaction was complete, the reaction mixture was concentrated under reduced pressure to give crude products. The crude products were purified by silica column chromatography (eluting with PE:EA=6:1-3:1, v/v) to give compounds 4a-4j.

4.1

Compound 4a, colorless oil, yield: 35.1%. $^1$H NMR (400 MHz, CDCl$_3$): δ 7.712-7.73 (m, 2H), 7.40-7.45 (m, 3H), 5.29-5.31 (m, 1H), 4.09 (d, J=17.5 Hz, 1H), 3.95-4.05 (m, 2H), 3.53 (d, J=17.5 Hz, 1H), 3.17 (d, J=4.7 Hz, 1H), 2.79-2.93 (m, 2H), 2.66-2.75 (m, 1H), 2.04 (s, 3H), 2.04 (s, 3H), 1.42-1.61 (m, 3H), 1.24-1.30 (m, 1H), 1.19 (d, J=7.0 Hz, 3H). $^{13}$C NMR (100 MHz, CDCl$_3$): δ 191.24, 171.76, 171.16, 157.79, 151.09, 139.32, 130.33, 128.82, 128.26, 127.17, 89.10, 76.70, 64.09, 52.67, 36.68, 33.87, 33.47, 30.01, 27.50, 21.69, 20.98, 19.12.

4.2

Compound 4b, colorless oil, yield: 33.6%. $^1$H NMR (400 MHz, CDCl$_3$): δ 7.73-7.78 (m, 2H), 7.13-7.17 (m, 2H), 5.30-5.33 (m, 1H), 4.08 (d, J=17.5 Hz, 1H), 3.96-4.09 (m, 2H), 3.53 (d, J=17.5 Hz, 1H), 3.18 (d, J=4.7 Hz, 1H), 2.81-2.95 (m, 2H), 2.68-2.77 (m, 1H), 2.06 (s, 6H), 1.43-1.62 (m, 3H), 1.22-1.29 (m, 1H), 1.21 (d, J=7.0 Hz, 3H). $^{13}$C NMR (100 MHz, CDCl$_3$): δ 190.20, 171.65, 171.09, 164.21 (d, J=250.4 Hz), 156.82, 151.13, 139.34, 129.26, 129.18, 124.57 (d, J=3.1 Hz), 116.12, 115.90, 89.21, 75.06, 64.02, 52.60, 36.72, 33.86, 33.45, 30.02, 27.53, 21.67, 20.94, 19.08.

4.3

Compound 4c, colorless oil, yield: 50.4%. $^1$H NMR (400 MHz, CDCl$_3$): δ 7.67 (d, J=8.5 Hz, 2H), 7.41 (d, J=8.5 Hz, 2H), 5.28-5.31 (m, 1H), 4.06 (d, J=17.5 Hz, 1H), 3.94-4.07 (m, 2H), 3.50 (d, J=17.5 Hz, 1H), 3.16 (d, J=4.7 Hz, 1H), 2.79-2.93 (m, 2H), 2.66-2.75 (m, 1H), 2.04 (s, 6H), 1.40-1.63 (m, 3H), 1.22-1.29 (m, 1H), 1.19 (d, J=7.0 Hz, 3H). $^{13}$C NMR (100 MHz, CDCl$_3$): δ 191.17, 171.63, 171.16, 156.91, 151.25, 139.32, 136.87, 129.14, 128.42, 126.79, 89.35, 75.11, 64.05, 52.55, 36.50, 33.84, 33.47, 29.99, 27.53, 21.71, 20.99, 19.11.

4.4

Compound 4d, colorless oil, yield: 63.6%. $^1$H NMR (400 MHz, CDCl$_3$): δ 7.58 (d, J=8.6 Hz, 4H), 5.28-5.30 (m, 1H), 4.06 (d, J=17.3 Hz, 1H), 3.94-4.07 (m, 2H), 3.50 (d, J=17.4 Hz, 1H), 3.15 (d, J=4.8 Hz, 1H), 2.79-2.93 (m, 2H), 2.65-2.74 (m, 1H), 2.04 (s, 6H), 1.40-1.63 (m, 3H), 1.22-1.30 (m, 1H), 1.19 (d, J=7.0 Hz, 3H). $^{13}$C NMR (100 MHz, CDCl$_3$): δ 191.14, 171.60, 171.14, 157.00, 151.25, 139.30, 132.09, 128.60, 127.22, 125.21, 89.36, 75.11, 64.03, 52.52, 36.43, 33.83, 33.46, 29.99, 27.53, 21.70, 20.99, 19.09.

4.5

Compound 4e, colorless oil, yield: 57%. $^1$H NMR (400 MHz, CDCl$_3$): δ 7.86 (d, J=8.4 Hz, 2H), 7.74 (d, J=8.4 Hz, 2H), 5.30-5.32 (m, 1H), 4.09 (d, J=17.5 Hz, 1H), 3.94-4.15 (m, 2H), 3.53 (d, J=17.5 Hz, 1H), 3.17 (d, J=4.7 Hz, 1H), 2.81-2.95 (m, 2H), 2.66-2.75 (m, 1H), 2.04 (s, 3H), 2.04 (s, 3H), 1.43-1.62 (m, 3H), 1.22-1.29 (m, 1H), 1.19 (d, J=7.0 Hz, 3H). $^{13}$C NMR (100 MHz, CDCl$_3$): δ 190.97, 171.36, 171.16, 156.57, 151.50, 139.27, 132.57, 127.67, 118.18, 114.16, 89.89, 75.18, 63.99, 52.39, 36.06, 33.79, 33.48, 29.94, 27.59, 21.74, 21.05, 20.99, 19.08.

4.6

Compound 4f, colorless oil, yield: 26.8%. $^1$H NMR (400 MHz, CDCl$_3$): δ 7.63 (d, J=8.2 Hz, 2H), 7.25 (d, J=8.2 Hz, 2H), 5.30-5.33 (m, 1H), 4.01 (d, J=17.4 Hz, 1H), 3.97-4.08 (m, 2H), 3.52 (d, J=17.4 Hz, 1H), 3.18 (d, J=4.8 Hz, 1H), 2.80-2.94 (m, 2H), 2.68-2.77 (m, 1H), 2.42 (s, 3H), 2.06 (s, 3H), 2.05 (s, 3H), 1.42-1.67 (m, 3H), 1.25-1.34 (m, 1H), 1.21 (d, J=7.0 Hz, 3H). $^{13}$C NMR (100 MHz, CDCl$_3$): δ

191.29, 171.81, 171.09, 157.70, 150.94, 141.10, 139.36, 129.49, 127.09, 125.45, 88.93, 75.03, 64.08, 52.70, 36.79, 33.89, 33.45, 30.06, 27.49, 21.65, 21.47, 20.94, 19.10.

4.7

Compound 4g, colorless oil, yield: 52.9%. $^1$H NMR (400 MHz, CDCl$_3$): δ 7.66 (d, J=8.8 Hz, 2H), 6.94 (d, J=8.8 Hz, 2H), 5.28-5.31 (m, 1H), 4.05 (d, J=17.4 Hz, 1H), 3.94-4.06 (m, 2H), 3.85 (s, 3H), 3.50 (d, J=17.4 Hz, 1H), 3.15 (d, J=4.8 Hz, 1H), 2.78-2.92 (m, 2H), 2.67-2.73 (m, 1H), 2.04 (s, 3H), 2.03 (s, 3H), 1.40-1.63 (m, 3H), 1.22-1.29 (m, 1H), 1.20 (d, J=7.0 Hz, 3H). $^{13}$C NMR (100 MHz, CDCl$_3$): δ 191.37, 171.91, 171.18, 161.59, 157.33, 151.05, 139.33, 128.77, 120.76, 114.23, 88.84, 75.06, 64.10, 55.40, 52.72, 36.88, 33.47, 30.01, 27.50, 21.70, 21.00, 19.14.

4.8

Compound 4h, colorless oil, yield: 47.6%. $^1$H NMR (400 MHz, CDCl$_3$): δ 8.3 (d, J=9.0 Hz, 2H), 7.93 (d, J=9.0 Hz, 2H), 5.30-5.33 (m, 1H), 4.12 (d, J=17.5 Hz, 1H), 3.94-4.08 (m, 2H), 3.57 (d, J=17.5 Hz, 1H), 3.19 (d, J=4.7 Hz, 1H), 2.82-2.95 (m, 2H), 2.67-2.76 (m, 1H), 2.05 (s, 3H), 2.04 (s, 3H), 1.40-1.63 (m, 3H), 1.22-1.29 (m, 1H), 1.20 (d, J=7.0 Hz, 3H). $^{13}$C NMR (100 MHz, CDCl$_3$): δ 190.93, 171.31, 171.16, 156.33, 151.52, 148.94, 139.28, 134.30, 128.02, 124.06, 90.04, 76.71, 63.97, 52.36, 36.13, 33.79, 33.48, 29.96, 27.60, 21.73, 20.98, 19.07.

4.9

Compound 4i, colorless oil, yield: 18.3%. $^1$H NMR (400 MHz, CDCl$_3$): δ 8.73 (d, J=5.4 Hz, 2H), 7.66 (d, J=6.0 Hz, 2H), 5.30-5.33 (m, 1H), 4.08 (d, J=17.6 Hz, 1H), 3.93-4.10 (m, 2H), 3.53 (d, J=17.6 Hz, 1H), 3.18 (d, J=4.7 Hz, 1H), 2.81-2.95 (m, 2H), 2.66-2.75 (m, 1H), 2.04 (s, 6H), 1.40-1.63 (m, 3H), 1.22-1.29 (m, 1H), 1.19 (d, J=7.0 Hz, 3H). $^{13}$C NMR (100 MHz, CDCl$_3$): δ 190.86, 171.24, 171.20, 156.24, 151.50, 149.76, 139.27, 136.42, 121.25, 124.06, 90.07, 76.19, 63.98, 52.34, 35.68, 33.77, 33.50, 29.93, 27.60, 21.74, 19.09, 17.46.

Example 5: Inhibitory Effect of the Compounds on Leukotriene C4 (LTC4) Production in Mouse Bone Marrow-Derived Mast Cells (BMMCs)

5.1 Extraction of BMMCs (1) Experimental Animal: a 6-week-old female Balb/C mouse without specific pathogens.

(2) Extraction Process: the mouse was sacrificed by cervical dislocation. After confirming the death of the mouse, it was immersed in alcohol for 3-5 minutes. The back skin of the mouse was cut with tweezers and scissors on a clean bench. The spleen was removed and placed in a filter. The filter was placed in a petri dish containing serum-free medium. The spleen was grounded into a cell suspension having a cell concentration of 2×10$^6$ cells/mL. 2.5 g/mL of lectins was added, and cell suspension was then cultured in RPMI1640 medium for 5 days. The supernatant was collected. The femur bone of the mouse was removed, and joints of the bone was cut. The bone marrow was washed into a centrifuging tube by using serum-free medium. The bone marrow containing medium was then centrifuged, and the supernatant was discarded and the pellet was red bone marrow.

(3) Cell Culture: The cells were cultured for 4 weeks with RPMI1640, 10% Gibco FBS, 20% spleen supernatant, 1% AEPS, 1% MEM, and 1% double antibody.

5.2 MTT Assay to Determine the Non-cytotoxic Concentration of Compounds (1) Preparation of MTT Solution: 5 mg/mL MTT solution was prepared by weighing an amount of MTT ((2-(4,5-dimethyl-2-thiazolyl)-3,5-diphenyl-2H-tetrazole hydrobromide) and dissolving MMT in PBS (solvent), and the solution was then filtered using a 0.22 μm microporous membrane. The solution was light yellow and stored at −20° C.

(2) Method: BMMCs were seeded in 96-well plates at a density of 2×10$^5$/mL at 100 μL per well, and the compounds of different concentrations were added. 100 μL culture medium and 100 μL PBS were used as blank control. After 7 hours, 20 μL MMT (5 mg/mL) was added to each well. The plates were then placed in an incubator (5% CO$_2$, 37° C.) for 4 hours. After the reaction was complete, the supernatant was discarded, and 150 μL of DMSO was added to each well. After mixing, the absorbance (OD value) was measured at 490 nm using a microplate reader.

Cell Viability=$(OD_{compounds}-OD_{culture\ medium})/(OD_{PBS}-OD_{culture\ medium})\times 100\%$ The inhibition rates on the growth of BMMCs of the compounds at 10 μM are shown in Table 2.

TABLE 2

Inhibition of the Growth of BMMCs by the Compounds (10 μM)

| Compounds | Cell Toxicity (%) |
| --- | --- |
| 2a | 5.98 |
| 2b | 1.47 |
| 2c | 1.88 |
| 2d | 1.06 |
| 2e | −0.66 |
| 2f | −1.06 |
| 2g | 7.37 |
| 2h | 20.64 |
| 2i | 4.26 |
| 2j | −0.9 |
| OABL | 3.46 |
| 3a | 5.98 |
| 3b | −1.97 |
| 3c | −6.22 |
| 3d | 9.58 |
| 3e | 0.25 |
| 3f | 4.1 |
| 3g | 11.12 |
| 3h | 6.63 |
| 3i | 9.58 |
| 3j | 21.95 |
| 4a | 0.16 |
| 4b | −8.44 |
| 4c | 2.95 |
| 4d | −4.59 |
| 4e | 3.19 |
| 4f | −0.66 |
| 4g | 5.81 |
| 4h | 5.65 |
| 4i | 9.09 |
| ABL | 1.15 |

5.3 Effects of the Compounds on the Release of Inflammatory Factor LTC$_4$ from BMMCs Principle: This experiment is based on the competitive binding of LTC$_4$ to the LTC4-acetylcholinesterase conjugate (LTC$_4$ tracer) to determine the amount of LTC4 antiserum. Because the concentration of the LTC$_4$ tracer is constant and the concentration of LTC$_4$ is varied, the amount of LTC$_4$ tracer bound to the LTC$_4$ antiserum is inversely proportional to the amount of LTC$_4$. The antibody-LTC4 complex binds to the murine monoclonal anti-rabbit IgG, while the murine monoclonal anti-rabbit IgG has previously been conjugated to the kit. After the reaction system was stabilized, the unbound reagent was washed away. Ellman's reagent (a substrate containing acetylcholinesterase) was added. The enzymatic reaction had a distinct yellow reaction, strong absorption at 405 nm. The color depth was measured by the spectrophotometric method, and is proportional to the amount of $LTC_4$ tracer, which is inversely proportional to the amount of $LTC_4$.

(2) Methods:

(a) Sample Preparation: culturing mature BMMCs, adding IgE overnight, washing with PBS three times, and then spreading in 96-well plates ($1\times10^6$ cells/well). The test compound solutions were added to plates and the plates were incubated for 1-1.5 hours, stimulating with DNP-HSA for 15 min. The solutions were then centrifuged at 3000 rpm for 3 min at 4° C., and the supernatant was collected and diluted 5-fold with RPMI 1640 to obtain sample solution.

(b) ELISA Kit Reaction: Adding reagents according to the kit instructions, reacting at 4° C. for 18 h, and washing with washing buffer. 200 μL of Ellman's reagent was added to each well, reacting for 40 min.

(c) Measurement of Absorbance: The absorbance was measured at 405 nm.

(3) Results

The inhibition rates of the compounds for the production of $LTC_4$ by BMMCs at a concentration of 10 μM are shown in Table 3.

TABLE 3

Inhibition Rate (%) of the Compounds on $LTC_4$ production by BMMCs (10 μM)

| Compounds | Inhabitation Rate (%) |
|---|---|
| 2a | 69.36 |
| 2b | 77.46 |
| 2c | 67.43 |
| 2d | 50.4 |
| 2e | 85.49 |
| 2f | −32.88 |
| 2g | 0.91 |
| 2h | 87.14 |
| 2i | 84.84 |
| 2j | 74.36 |
| OABL | 53.24 |
| 3a | 79.15 |
| 3b | 89.01 |
| 3c | 70.16 |
| 3d | 89.94 |
| 3e | 93.95 |
| 3f | −23.48 |
| 3g | 93.19 |
| 3h | 84.4 |
| 3i | 88.7 |
| 3j | 88.7 |
| 4a | 21.93 |
| 4b | 32 |
| 4c | 84.4 |
| 4d | 97.77 |
| 4e | 88.22 |
| 4f | 28.77 |
| 4g | 53.28 |
| 4h | 92.79 |
| 4i | 83.53 |
| ABL | 35.21 |

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of inhibiting leukotriene comprising:
administrating a therapeutically effective amount of a compound of chemical formula I or II or a pharmaceutical acceptable salt thereof to a subject,

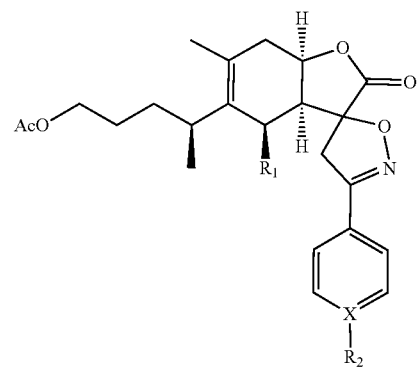

I

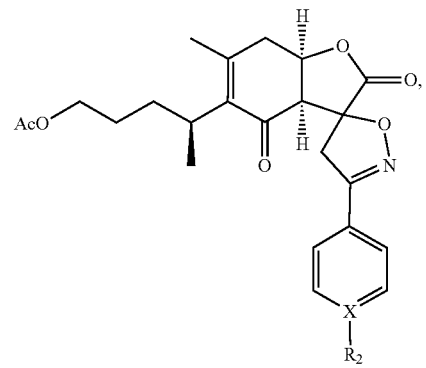

II wherein $R_1$ is OH or OAc; X is C or N; and $R_2$ is H, alkyl, alkoxy, benzyloxy, haloalkyl, OH, CN, $NO_2$, or halogen, provided that when X is N, $R_2$ is nil.

2. The method of claim 1, wherein X is C and $R_2$ is H, F, Cl, Br, CN, $CH_3$, $OCH_3$, $NO_2$ or OH.

* * * * *